United States Patent [19]

Chasan

[11] Patent Number: 5,496,304
[45] Date of Patent: Mar. 5, 1996

[54] SURGICAL MARKING PEN

[75] Inventor: Paul E. Chasan, Salt Lake City, Utah

[73] Assignee: University of Utah Research Foundation, Salt Lake City, Utah

[21] Appl. No.: 278,021

[22] Filed: Jul. 20, 1994

[51] Int. Cl.⁶ .................................................. A61B 17/00
[52] U.S. Cl. .............................. 606/1; 81/9.22; 606/116; 606/186; 604/47
[58] Field of Search .............................. 606/1, 116, 185, 606/186; 604/47, 48, 46; 101/19, 23, 24, 26; 81/9.22; 401/197, 208, 219

[56] References Cited

U.S. PATENT DOCUMENTS

| | | |
|---|---|---|
| 1,699,012 | 1/1929 | Naylor. |
| 4,392,493 | 7/1983 | Niemeijer. |
| 4,437,361 | 3/1984 | Steckel et al.. |
| 4,488,550 | 12/1984 | Niemeijer. |
| 4,608,045 | 8/1986 | Fretwell. |
| 4,665,912 | 5/1987 | Burton ........................... 606/186 |
| 4,671,277 | 6/1987 | Beuchat. |
| 4,796,624 | 1/1989 | Trott et al.. |
| 4,798,582 | 1/1989 | Sarath et al. ..................... 604/47 |
| 5,279,552 | 1/1994 | Magnet ............................ 81/9.22 |

FOREIGN PATENT DOCUMENTS 65858   7/1914   Germany .................... 81/9.22

Primary Examiner—Stephen C. Pellegrino
Assistant Examiner—Michael Peffley
Attorney, Agent, or Firm—Thorpe North & Western

[57] ABSTRACT

An apparatus and method are disclosed for marking the proper location of incisions to be made during a surgical procedure. The apparatus includes a member for penetrating inward of the outermost layer of the epidermis. A reservoir supplies a marking agent so that as the penetrating member penetrates the epidermis, marking agent is left inward of the outermost surface of the epidermis, thereby leaving a line which may be followed when making incisions during surgery. The method includes penetrating the outermost layer of the epidermis and leaving marking agent inward of the outermost layer of the epidermis. In a preferred embodiment of the method, a temporary marking agent, such as methylene blue, is used so that the line quickly disappears after surgery.

20 Claims, 5 Drawing Sheets

SURGICAL MARKING PEN

BACKGROUND OF THE INVENTION

The present invention relates to a marking pen, and in particular, to a marking pen for use during surgery so as to guide the surgeon in making a proper incision.

The use of marking pens during surgery is common. Often a surgeon will mark lines on a patient's body so as to know the proper place and length of the incision or incisions which will be made during the operation. Such lines can be particularly important in specialties such as plastic surgery where the operation is being conducted for cosmetic reasons. In such cases, it is extremely important that the incisions be at the proper location, and of the appropriate length. However, this is often difficult to do during surgery without the aid of markings.

Typically, a surgeon will use a felt tip pen to mark lines representing the desired incisions. Because of the patient's perspiration, natural oils and fluids that are used on the patient's body prior to surgery, such as antiseptic solutions, the lines made by the marking pens have a tendency to spread out or "bleed" after being made on the skin. Additionally, once an incision has been made, blood usually spills on the patient's skin, further blurring the lines. While attempts have been made to form the marking portions of the pen in a fine tip, blood and other fluids cause the ink to spread, thereby obscuring the original lines.

Another problem with the marking pens of the prior art is that they have a tendency to dry out. Some pens dry out in the package and others dry out after a single use. Additionally, the felt tip of the pen can get "gummed up" with the betadine used on the patient. Because of these problems, many surgeons have been known to break open a pen and use the ink reservoir inside the pen to draw the lines. The reservoir, however, is fairly broad and results in a substandard marking.

Due to these problems with marking pens, some surgeons rely on primitive marking techniques. For example, some doctors will dip toothpicks or similar instruments in methylene blue. The toothpick, etc., is then dragged across the patient's skin to form a line. The toothpicks, however, will not hold a significant amount of the marking agent and must be repeatedly dipped when the surgeon is drawing a number of lines.

To overcome these problems, there is a need for a marking pen which enables a surgeon to make a thin line on the patient's skin which will not significantly broaden or smear. Additionally, the line made by the marking pen should be temporary so that it will disappear shortly after the surgery has been completed.

SUMMARY OF THE INVENTION

It is an object of the present invention to provide a marking pen for use in operating room and the like which will produce a thin line on a patient's skin, thereby enabling a surgeon to make an appropriate incision.

It is another object of the present invention to provide a marking pen which will produce lines which will not smear or blur during surgery.

It is an additional object of the present invention to provide a marking pen which will not quickly dry out if left without a cap on the marking portion.

It is an additional object of the present invention to provide a manner in which the surgeon can determine if there is sufficient fluid in the marking pen to make the appropriate markings.

The above and other objects of the invention are achieved in a marking pen having a handle, and a fluid reservoir in fluid communication with a penetrating member, such as a pinwheel. The pinwheel, for example has a plurality of needles for puncturing at least one outer layer of the epidermis. As the pinwheel is rolled across a patient's skin, the pinwheel leaves a temporary tattooed line which may be used by the surgeon to make an accurate incision.

In an alternate embodiment of the invention, a continuous cutting surface is provided to extend through part of the epidermis, while a reservoir provides a marking agent to be disposed within the incision formed by the cutting surface.

In accordance with one aspect of the alternate embodiment, the continuous cutting surface rotates as the incision is being made. In accordance with another aspect of the invention, the cutting surface is stationary.

BRIEF DESCRIPTION OF THE DRAWINGS

The above, and other objects, features and advantages of the invention, will become apparent from a consideration of the following detailed description presented in connection with the accompanying drawings, in which.

DETAILED DESCRIPTION

Figure 1:
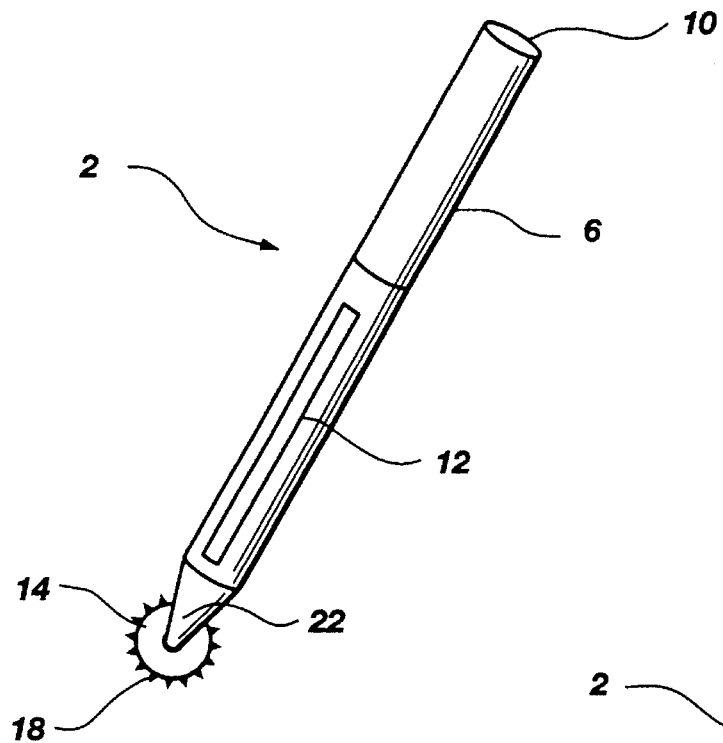
FIG. 1 shows a perspective view of a surgical marking pen made in accordance with the present invention.

Reference will now be made to the drawings in which the various elements of the present invention will be given numeral designations and in which the invention will be discussed so as to enable one skilled in the art to make and use the invention. Referring to FIG. 1, there is shown a surgical marking pen, generally indicated at 2, for marking lines on a patient's body prior to, or during surgery. The marking pen 2 has a body 6 which is analogous to other marking pens in that the body contains a reservoir (not shown) for holding a supply of a marking agent, such as ink. The marking pen 2 may be disposable, or refillable through a cap, such as cap 10. Disposed in the side of the handle 6 is a window 12 to enable a user to tell if the marking pen 2 is running out of marking agent.

Attached to an end of the marking pen 2 is a pinwheel 14 with a plurality of needles 18. As will be explained in further detail below, the needles 18 allow a patient to be marked with fine lines which do not blur or smudge during surgery.

The pinwheel 14 is attached to the pen body 6 by a pair of arms 22.

The marking agent in the reservoir (not shown) passes through the arms and into the pinwheel 14. As the pinwheel 14 is run over a patient's body, the needles 18 make small perforations in the patient's epidermis and deposit small amounts of the marking agent. Because the marking agent is retained beneath the surface of the skin, it is minimally affected by smearing agents such as sweat, blood, grease and antiseptic solutions. As will be explained below, the marking agent is preferably temporary (i.e. biodegradable) such that the patient is not left with a prolonged tattoo marking the desired incision.

In use, the marking pen 2 can be held in the surgeon's hand in the same manner as a conventional marking pen, or in the same manner as a knife. As the pinwheel 14 is run across the desired point of incision, the needles 18 will leave fine dots or marks which generally form a line. By following the line, the surgeon can be assured that he or she is making the proper incision.

Figure 2:
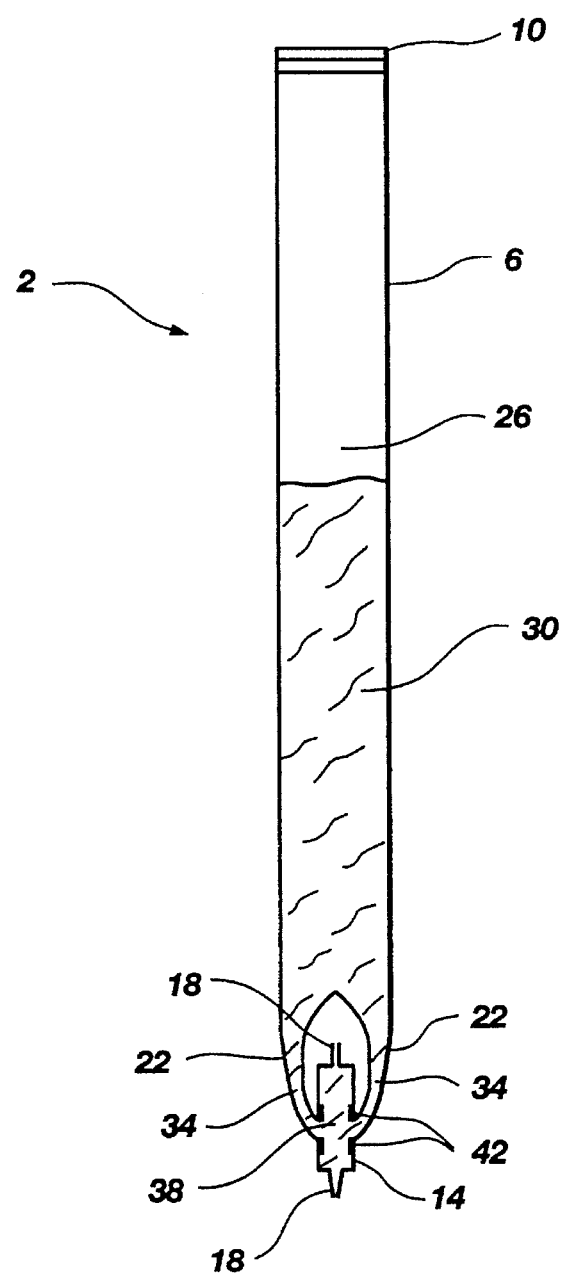
FIG. 2 shows a front cross-sectional view of the surgical marking pen revealing an interior reservoir for holding a marking agent.

Referring now to FIG. 2, there is shown a cross-sectional view of the marking pen 2. As was stated above, the pen body 6 is hollow, so as to form a reservoir 26. The reservoir 26 holds a quantity of marking agent 30, such as methylene blue. Methylene blue is particularly useful in that it is temporary and is not harmful to the patient. Those skilled in the art will be familiar with other marking agents which currently exist and additional agents when they are developed.

The marking agent 30 flows through a hollow portion 34 of each arm 22 in a preferred embodiment. However, it would be a simple modification to cause the marking agent 30 agent to flow through a single arm, or to have only one arm support the pinwheel 14. The marking agent 30 passes from the arms 22 into a central section 38 of the pinwheel 14. As shown in FIG. 2, each arm 22 can have a flange 42 extends into the pinwheel and holds the arms in secure attachment with the pinwheel 14. The flanges 42 also prevent the marking agent 30 from leaking out from the sides of the central section 38 of the pinwheel 14. Those skilled in the art will recognize several ways in which the arms 22 could be attached to the pinwheel 14 so as to prevent leakage of the marking agent 30 as the pinwheel rotates.

Figure 3:
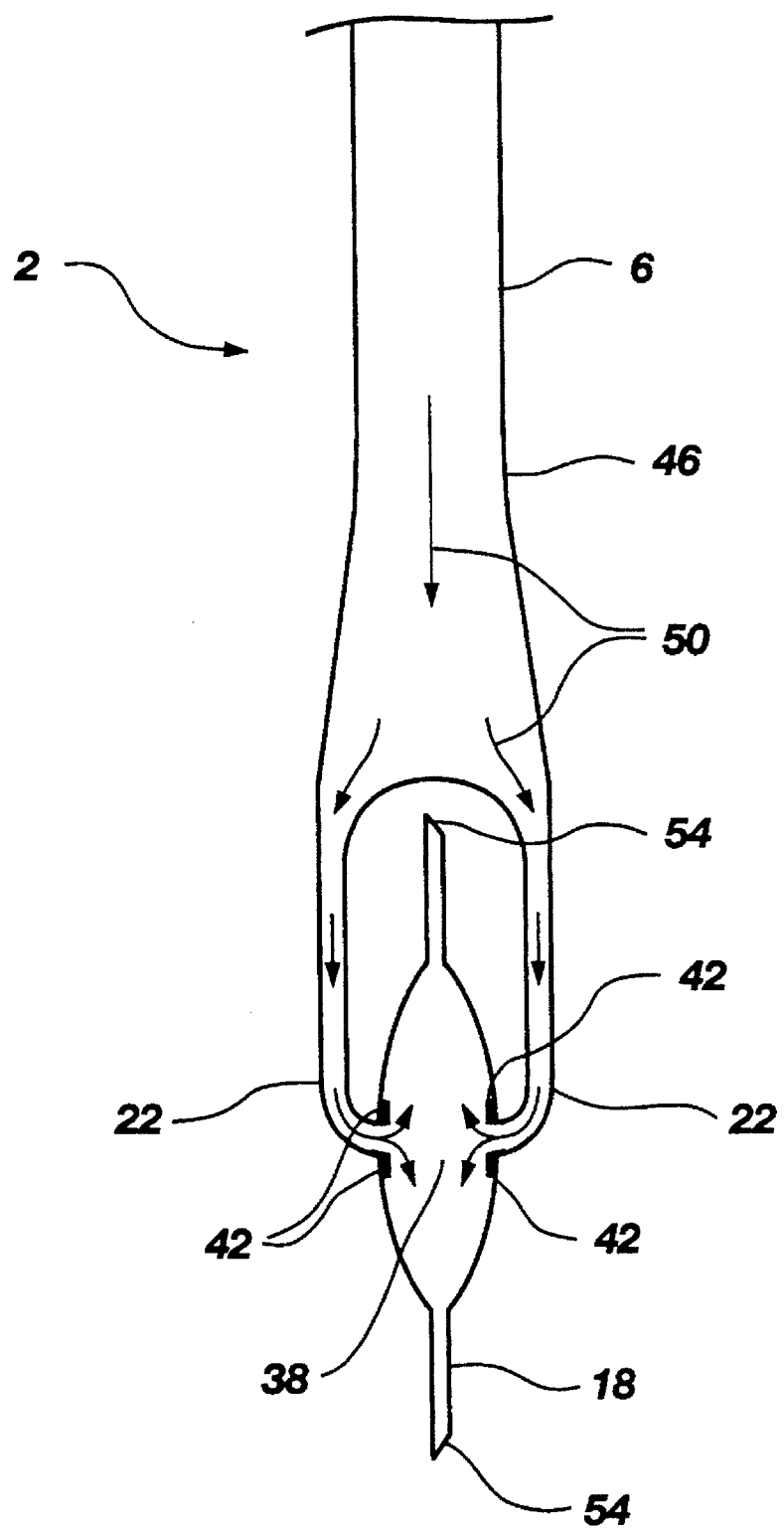
FIG. 3 shows a close-up view of the lower portion of the pen shaft and the pinwheel used to make lines for surgical procedures.

Referring now to FIG. 3, there is shown a fragmented close-up view of a lower portion 46 of another embodiment of the marking pen 2. Arrows 50 are positioned within the pen body 6 to show the flow direction of the marking agent (not shown). As the marking agent passes from the arms 22, into the central portion 38 of the pinwheel 14, the rotating pinwheel causes the marking agent (not shown) to flow toward the needles 18. Each needle has a sharp, hollowed point 54 which will pierce an outer layer of skin and leave a small drop of the marking agent, such as methylene blue.

While not shown in FIGS. 2–3, the pen body 6 could be transparent, so as to allow a surgeon or other medical personnel to see when the marking pen 2 was low on marking agent. When the pen 2 is low, it can either be replaced, or refilled by using the cap 10 (FIGS. 1 and 2).

Figure 4:
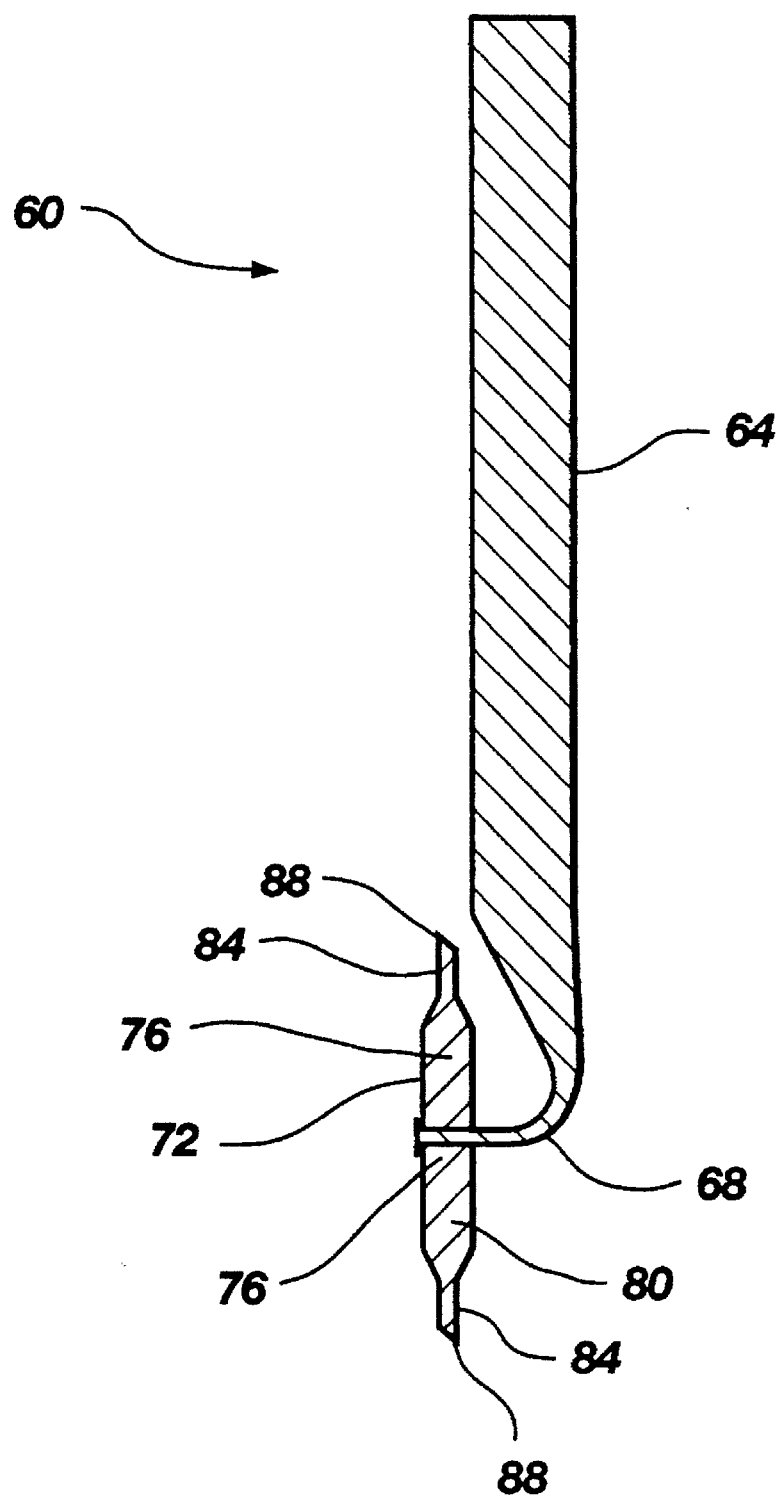
FIG. 4 shows an alternate embodiment of the marking pen of the present invention.

Referring now to FIG. 4, there is shown an alternate embodiment of the present invention. Because of the increasing fear that communicable diseases will be spread from one patient to another by reuse of medical equipment, it is often desirable to use a disposable pen to mark the patient. This is particularly true when the marking pen, as with the present invention, punctures the epidermis of the patient. Thus, in FIG. 4, there is shown a disposable marking pen, generally indicated at 60. The pen 60 includes a handle portion 64 which is connected by an arm 68 to a pinwheel 72. The pinwheel 72 includes a central portion 76 which acts as a reservoir and stores a marking agent 80. Radially outward from the central portion 76 are a plurality of needles 84 with sharp, hollow ends 88 which make small perforations in the epidermis and leave a small amount of marking agent 80 with each puncture. As the pinwheel 72 rolls, it leaves a dotted line which may be used by a surgeon for making the incision in the desired place.

Obviously, the disposable marking pen 60 contains considerably less marking agent 80 than the marking pen 2 shown in FIGS. 1–3. Such a pen 60 will typically be used when the incision which needs to be cut is relatively small. However, it will be apparent that the pinwheel 72 could be enlarged to hold additional marking agent 80.

To prevent the pen 60 from drying out, a plurality of caps could be made available to place on the needles 84. In most situations, however, the pen 60 will be used primarily at the beginning of surgery and will be disposed of before the supply of marking agent has a chance to dry up.

Figure 5:
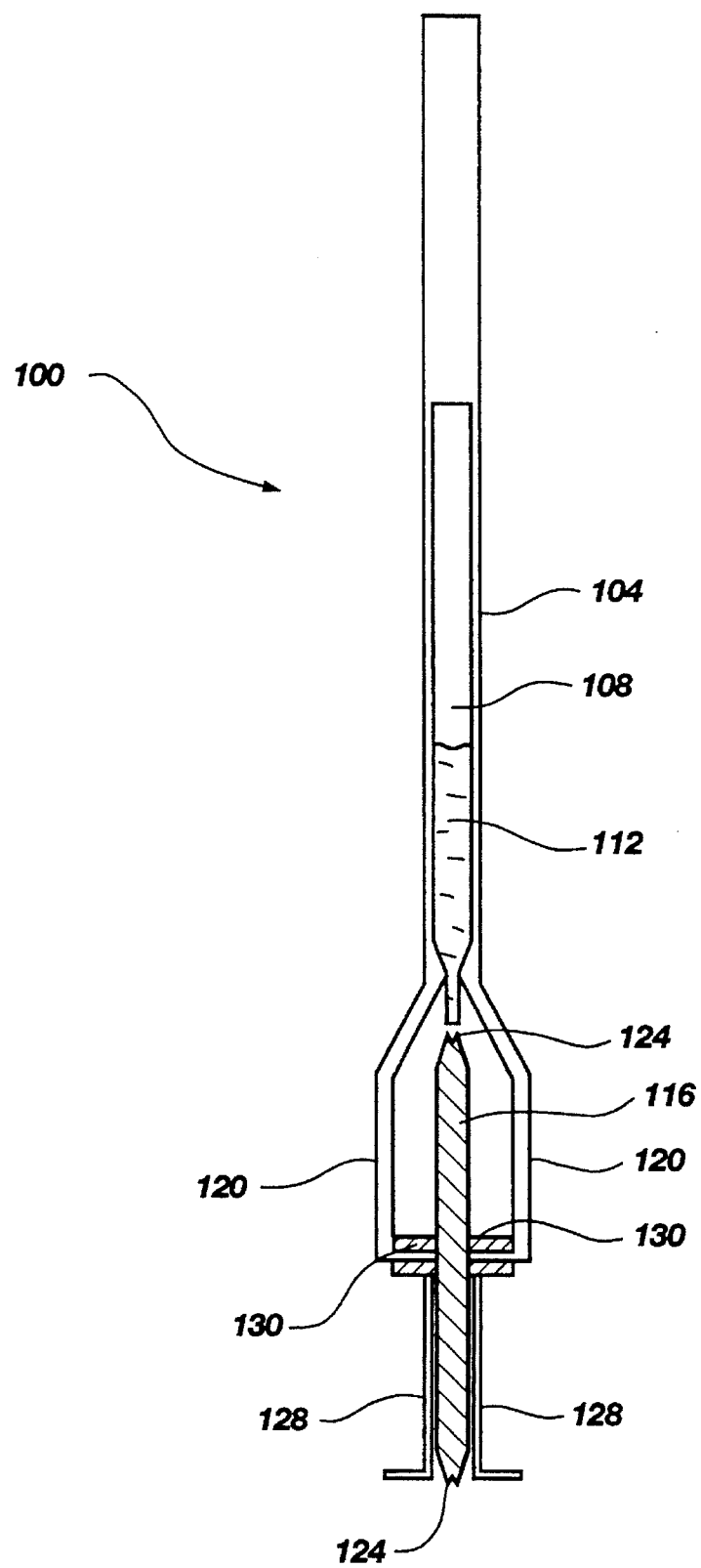
FIG. 5 shows a close-up, cross-sectional view of another embodiment of the present invention, in which the cutting surface is a rotating blade instead of the pinwheel shown in FIGS. 1 through 4.

Referring now to FIG. 5, there is shown a frontal, cross-sectional view of an alternate embodiment of a marking pen, generally indicated at 100. The pen 100 includes a handle 104 which is generally hollow to form a reservoir 108 for holding a marking agent 112, such as methylene blue, brilliant green and Jenslon Violate. The pen 100 also includes a circular cutting blade 116 which is rotatably connected to the handle 104 by two arms 120. In use, the cutting blade 116 rotates about an axis extending between the two arms 120. As the cutting blade 116 rotates, the reservoir 108 drops small amounts of the marking agent 112 into a groove 124 formed in the cutting blade. As the cutting blade 116 passes beneath the outer surface of the epidermis, marking agent 112 is left below the surface of the epidermis, thereby leaving a line for the surgeon to follow when making the subsequent incision. While the present embodiment shows the groove 124 in the cutting blade 116, those skilled in the art will recognize that there are many different ways for administering the marking agent 112 below the surface of the skin.

A pair of flanges 128 are positioned adjacent to the cutting blade 116 to prevent the blade from cutting through the epidermis. Ideally, the blade 116 will cut one to two layers deep so as to minimize the probability of causing the skin to bleed following the cut.

As shown in FIG. 5, the pen 100 also includes a washer 130 disposed on either side of the cutting blade 116. The washers 130 help center the cutting blade 116, and can be used to support the flanges 128.

Figure 6:
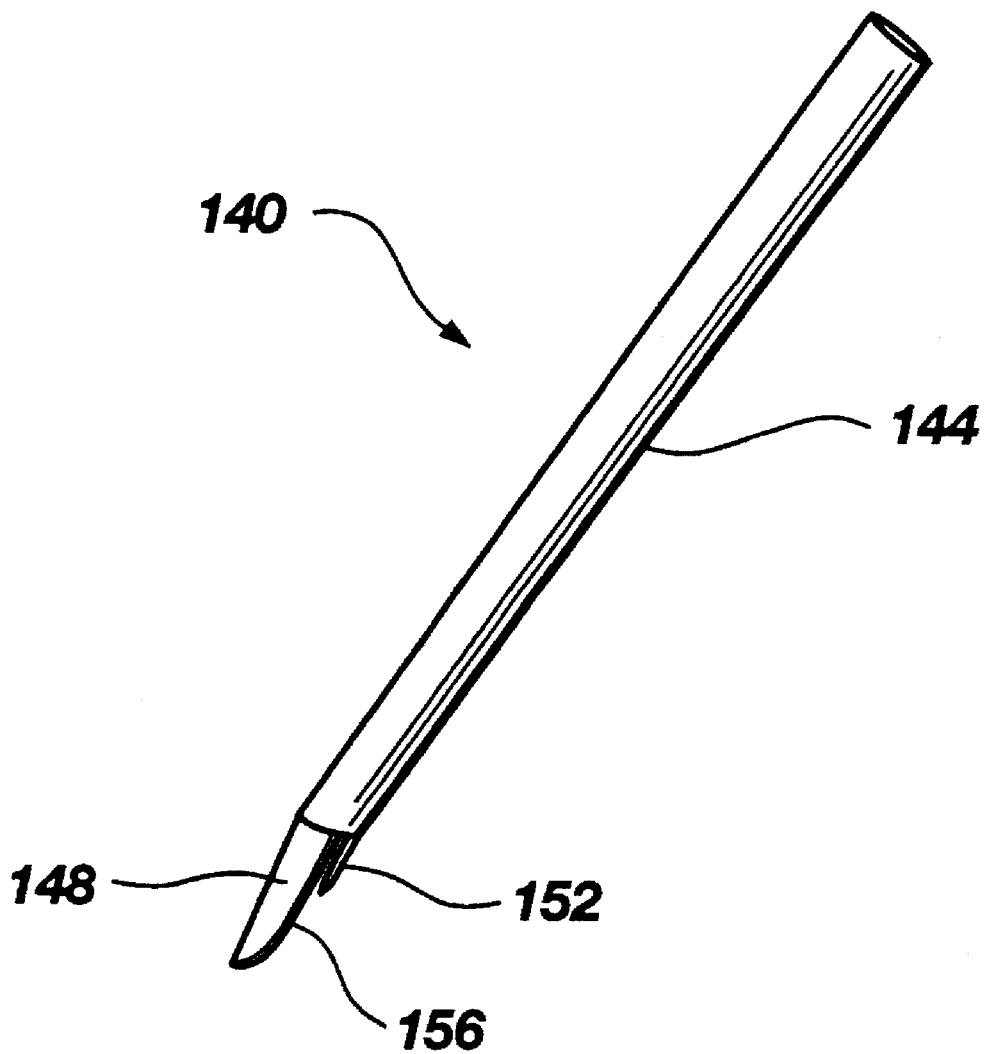
FIG. 6 shows yet another embodiment of the present invention, in which the cutting surface is a blade which is stationary relative to the handle.

Referring now to FIG. 6, there is shown an elevated perspective view of yet another embodiment of a marking pen, generally indicated at 140. The pen 140 includes a handle 144 and a cutting blade 148 which are connected to one another. Inside the handle 144 is a reservoir (not shown) for holding a marking agent. A small tube 152 extends to a cutting edge 156 of the cutting blade 148 and delivers a small amount of marking agent to the cutting edge. As the cutting edge 156 penetrates the outer layer of the epidermis, the marking agent is left so as to form a line which can later be used when making the incision during the operation.

As with the embodiment shown in FIG. 5, the cutting blade 148 could also have a flange to prevent the cutting edge 156 from extending too deeply into the epidermis. Those skilled in the art will recognize several different methods for mounting such a flange on the cutting blade, or the handle, so as to limit the depth of any cuts to the outer layers of the epidermis.

By making small perforations or incisions in the skin, the deposited marking agent is less susceptible to smudging, blurring, or other distortions which may interfere with the ability of the surgeon to make the incision in the proper place. Such an ability is particularly important in specialty fields, such as plastic surgery, where exact location of the incision is important. When using a conventional marker, the incision can be erroneous by an eighth of an inch or more, due to the bleeding or smudging of the ink. By placing a very fine temporary tattooed line along the desired cut, there is very little blurring or other distortion. If blood or other fluid comes on the line, it can be wiped off with minimal interference to the tattooed line. Thus, the surgeon is able to better perform his or her job.

In the manner described above, an apparatus and method is disclosed for marking lines on a patient's body to better enable a surgeon to make incisions in the appropriate place. It will be understood that other variations and modifications of the apparatus and method will be apparent to those skilled in the art without departing from the scope of the invention. The describe method and apparatus are not meant to be a delineation of the scope of the invention, but merely an example of embodiments thereof.

I claim:

1. A marking pen for indicating the proper location of incisions to be made on a patient undergoing surgery, the marking pen comprising:

rotatable penetrating means for penetrating a portion of the epidermis of the patient, the penetrating means including a means for depositing a marking agent within the epidermis;

reservoir means for storing the marking agent and for conveying the marking agent to the penetrating means; and wherein at least a portion of said reservoir means is disposed in the penetrating means; and handle means attached to the penetrating means so as to enable a user to roll the penetrating means across the epidermis of a patient, thereby leaving a line of marking agent in the epidermis.

2. The marking pen of claim 1, wherein the penetrating means comprises a pinwheel having a plurality of outwardly projecting needles in rotational alignment.

3. The marking pen of claim 2, wherein each of the needles has a hollow cutting point, each hollow cutting point being in fluid communication with the reservoir means.

4. The marking pen of claim 3, wherein at least a portion of the reservoir means is disposed within the handle means.

5. The marking pen of claim 4, wherein the handle means is connected to the pinwheel by a pair of arms, at least one of the arms comprising a channel for carrying marking agent from the reservoir disposed in the handle to the pinwheel.

6. The marking pen of claim 1, further comprising a marking agent of methylene blue contained within the reservoir means.

7. The marking pen of claim 1, wherein the penetrating means comprises a cutting blade.

8. The marking pen of claim 7, wherein the cutting blade comprises a disk having an annular cutting surface about an outer perimeter of the disk.

9. The marking pen of claim 8, wherein the cutting blade further comprises a groove formed in the cutting surface for carrying the marking agent from the reservoir means to the epidermis of the patient.

10. The marking pen of claim 7, wherein the marking pen further comprises a means for limiting the depth of penetration of the penetrating means within the epidermis.

11. The marking pen of claim 10, wherein the limiting means comprises a flange disposed adjacent to the cutting blade so as to limit the depth which the cutting blade can enter the epidermis.

12. The marking pen of claim 1, wherein penetrating means of the marking pen comprises a plurality of spaced apart, outwardly projecting members, such that the line of marking agent formed by the penetrating means is not continuous.

13. The marking pen of claim 1, further comprising a biodegradable marking agent.

14. A method for non-permanently marking the proper place for a surgical incision to be made on a patient's body with a marking pen means, the method comprising:

(a) making a plurality of penetrations in the patient's epidermis by rolling said marking pen means on the epidermis such that each penetration extends to a position between the innermost layer of the epidermis and the outermost surface of the epidermis; and (b) depositing a marking agent in each penetration so as to draw a locus of points representing a line along the patient's epidermis, thereby marking the location of an incision to be made on the patient.

15. The method for marking the proper place for a surgical incision to be made of claim 14, wherein step (b) comprises, more specifically, depositing a marking agent in each perforation so as to draw a dotted line along the patient's epidermis and mark the location of an incision to be made on the patient.

16. The method for marking the proper place for a surgical incision to be made of claim 15, comprising the more specific step of using a hollow needle to make the perforations and to deposit the marking agent inward of the outermost layer of the epidermis.

17. The method for marking the proper place for a surgical incision to be made of claim 16, comprising the more specific steps of positioning a plurality of hollow needles so as to form a rotatable pinwheel, rolling the pinwheel along the epidermis such that the needles contact the epidermis, and supplying marking agent while the pinwheel rotates so as to leave a dotted line as the pinwheel is rolled along the epidermis.

18. The method for marking the proper place for a surgical incision to be made of claim 14, wherein step (a) comprises, more specifically, using a rotating cutting blade to make an incision slightly below the outermost layer of the epidermis, and wherein step (b) comprises, more specifically, depositing a marking agent as the cutting blade makes the incision so as to draw a line along the patient's epidermis and mark the location of an incision to be made on the patient.

19. The method for marking the proper place for a surgical incision to be made of claim 14, wherein step (b) comprises depositing a temporary marking agent such that the line will disappear following surgery.

20. A marking pen for indicating the proper location of incisions to be made on a patient undergoing surgery, the marking pen comprising:

penetrating means for penetrating a portion of the epidermis of the patient, the penetrating means including a plurality of needles forming a pinwheel;

means for depositing a marking agent beneath an outermost surface of the epidermis, the depositing means being disposed adjacent to the penetrating means;

reservoir means for storing the marking agent and for conveying the marking agent to the depositing means within the pinwheel; and handle means attached to the penetrating means for enabling a user to move the penetrating means across the epidermis of a patient and deposit the marking agent beneath the outermost surface of the epidermis, thereby leaving a line in the epidermis.

* * * * *